(12) United States Patent
Wendland

(10) Patent No.: US 10,448,724 B1
(45) Date of Patent: Oct. 22, 2019

(54) BACK CREAM APPLICATOR

(71) Applicant: John Wendland, West Milford, NJ (US)

(72) Inventor: John Wendland, West Milford, NJ (US)

(*) Notice: Subject to any disclaimer, the term of this patent is extended or adjusted under 35 U.S.C. 154(b) by 78 days.

(21) Appl. No.: 15/811,868

(22) Filed: Nov. 14, 2017

(51) Int. Cl.
*A45D 34/04* (2006.01)
*A61M 35/00* (2006.01)
*A45D 34/00* (2006.01)
*A45D 40/28* (2006.01)

(52) U.S. Cl.
CPC ........... *A45D 34/04* (2013.01); *A61M 35/003* (2013.01); *A45D 40/28* (2013.01); *A45D 2034/005* (2013.01); *A45D 2200/1081* (2013.01)

(58) Field of Classification Search
CPC ...... A45D 34/04; A45D 34/042; A45D 40/28; A45D 2034/005; A45D 2200/1081; A61M 35/003; A47K 5/06
USPC .......................................... 401/6, 188 R, 187
See application file for complete search history.

(56) References Cited

U.S. PATENT DOCUMENTS

| | | | | |
|---|---|---|---|---|
| 1,485,126 A * | 2/1924 | Schumacher | ...... | A46B 11/0055 401/185 |
| 2,800,673 A * | 7/1957 | Lazisky | ......... | A45D 33/28 401/188 R |
| 5,240,339 A | 8/1993 | DeForest | | |
| 5,931,591 A | 8/1999 | McCracken | | |
| 6,129,469 A * | 10/2000 | Messer | ......... | A45D 34/042 401/6 |
| 6,213,672 B1 * | 4/2001 | Varga | ............. | A47L 13/20 15/144.4 |
| 6,247,862 B1 * | 6/2001 | Garza | ............. | A45D 34/04 401/187 |
| 6,412,997 B2 * | 7/2002 | Berke | ............. | A45D 34/04 401/138 |
| 6,543,954 B2 * | 4/2003 | Owings | ......... | A45D 34/04 401/185 |
| 6,726,385 B1 * | 4/2004 | Borowski | ...... | A46B 9/005 401/187 |
| D515,737 S | 2/2006 | Angeletta | | |
| 7,309,180 B2 | 12/2007 | Russell | | |
| 8,360,668 B1 * | 1/2013 | Hinnant | ......... | A46B 5/0075 401/188 R |
| 8,967,898 B1 * | 3/2015 | Dayeh | ............ | A47K 7/028 401/188 R |
| 8,998,523 B1 | 4/2015 | Muller | | |
| 10,188,199 B2 * | 1/2019 | Hilliard | ......... | A46B 5/005 |

(Continued)

*Primary Examiner* — Nicholas J. Weiss

(57) ABSTRACT

The back cream applicator is configured for use with a therapeutic liquid such as a lotion or cream. The back cream applicator applies the therapeutic liquid to a person. The back cream applicator is configured for self-application of the therapeutic liquid. The back cream applicator is configured to extend the reach of the person such that the therapeutic liquid can be applied to locations that are otherwise difficult to reach. The back cream applicator comprises a telescopic handle, a cleansing head, a pump, and a refillable reservoir. The cleansing head applies the therapeutic liquid to the person. The refillable reservoir contains a stock of the therapeutic liquid for use by the cleansing head. The pump is a mechanical device that transports the therapeutic liquid to the cleansing head. The telescopic handle is an extension apparatus that extends the reach of the person.

13 Claims, 4 Drawing Sheets

(56) References Cited

U.S. PATENT DOCUMENTS

2006/0008313 A1* 1/2006 Wisniewski ......... A45D 34/042
                                                    401/6
2007/0243005 A1   10/2007 Sviesa
2009/0092435 A1*  4/2009 Stevens ................. A45D 34/04
                                                    401/6
2015/0082567 A1*  3/2015 Perry .................... A47K 11/10
                                                    15/144.4

* cited by examiner

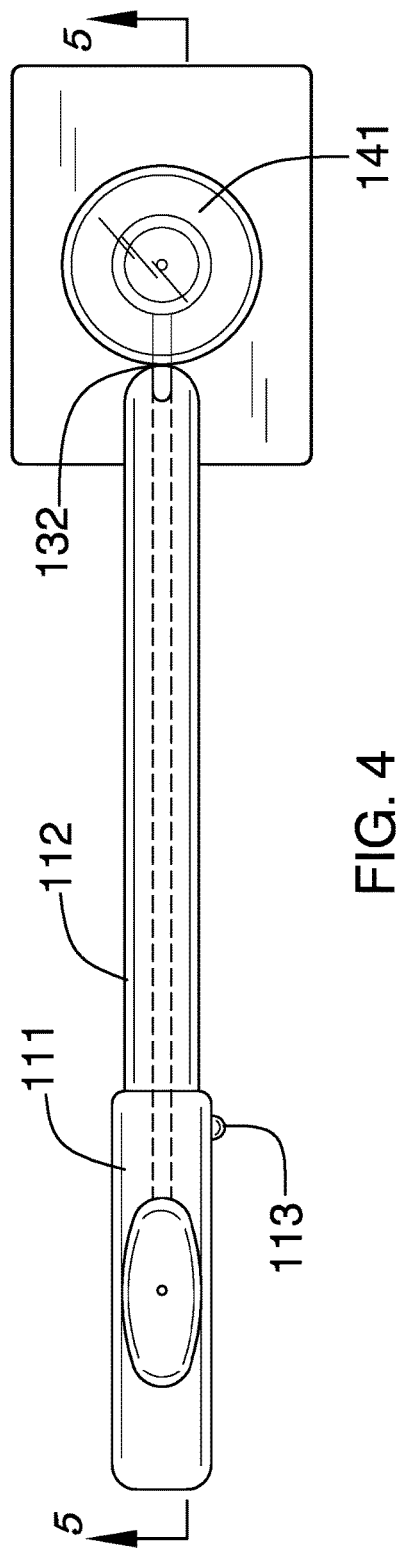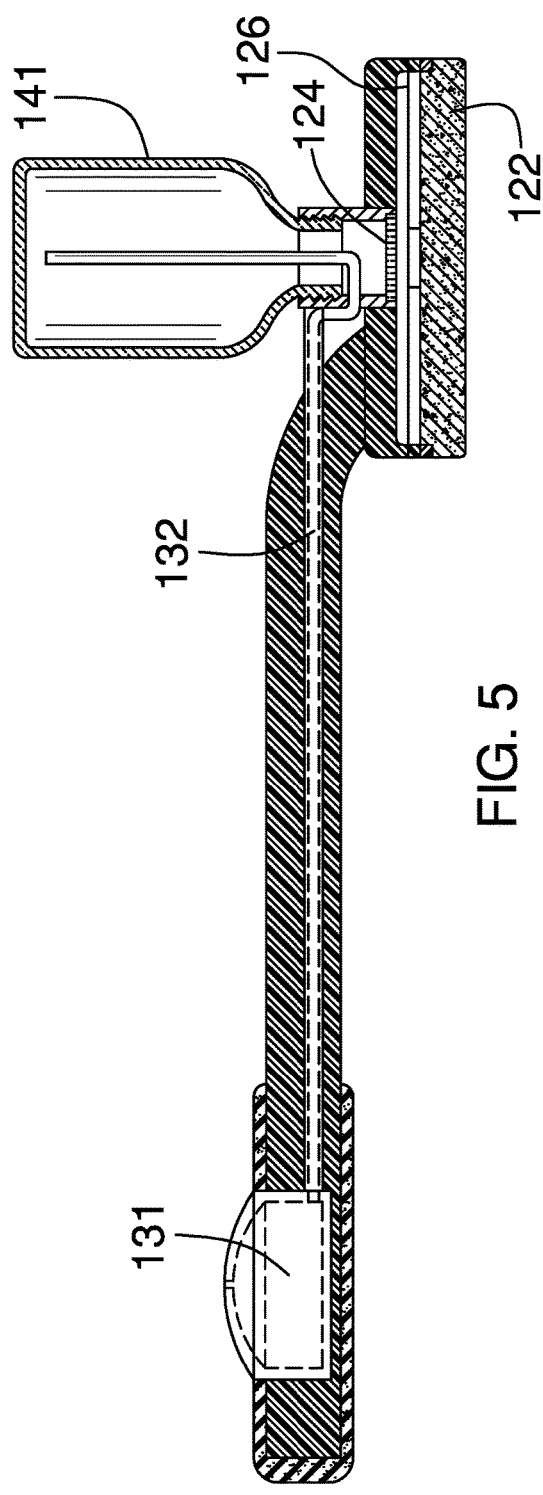

BACK CREAM APPLICATOR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal and domestic articles including shaving, hairdressing, and cosmetic treatment equipment, more specifically, an applicator comprising a pad.

SUMMARY OF INVENTION

The back cream applicator is configured for use with a therapeutic liquid such as a lotion or cream. The back cream applicator applies the therapeutic liquid to a person. The back cream applicator is configured for self-application of the therapeutic liquid. The back cream applicator is configured to extend the reach of the person such that the therapeutic liquid can be applied to locations that are otherwise difficult to reach. The back cream applicator comprises a telescopic handle, a cleansing head, a pump, and a refillable reservoir. The cleansing head applies the therapeutic liquid to the person. The refillable reservoir contains a stock of the therapeutic liquid for use by the cleansing head. The pump is a mechanical device that transports the therapeutic liquid to the cleansing head. The telescopic handle is an extension apparatus that extends the reach of the person.

These together with additional objects, features and advantages of the back cream applicator will be readily apparent to those of ordinary skill in the art upon reading the following detailed description of the presently preferred, but nonetheless illustrative, embodiments when taken in conjunction with the accompanying drawings.

In this respect, before explaining the current embodiments of the back cream applicator in detail, it is to be understood that the back cream applicator is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the back cream applicator.

It is therefore important that the claims be regarded as including such equivalent construction insofar as they do not depart from the spirit and scope of the back cream applicator. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 4 is a top view of an embodiment of the disclosure.

FIG. 5 is a cross-sectional view of an embodiment of the disclosure across 5-5 as shown in FIG. 4.

DETAILED DESCRIPTION OF THE EMBODIMENT

Figure 1:
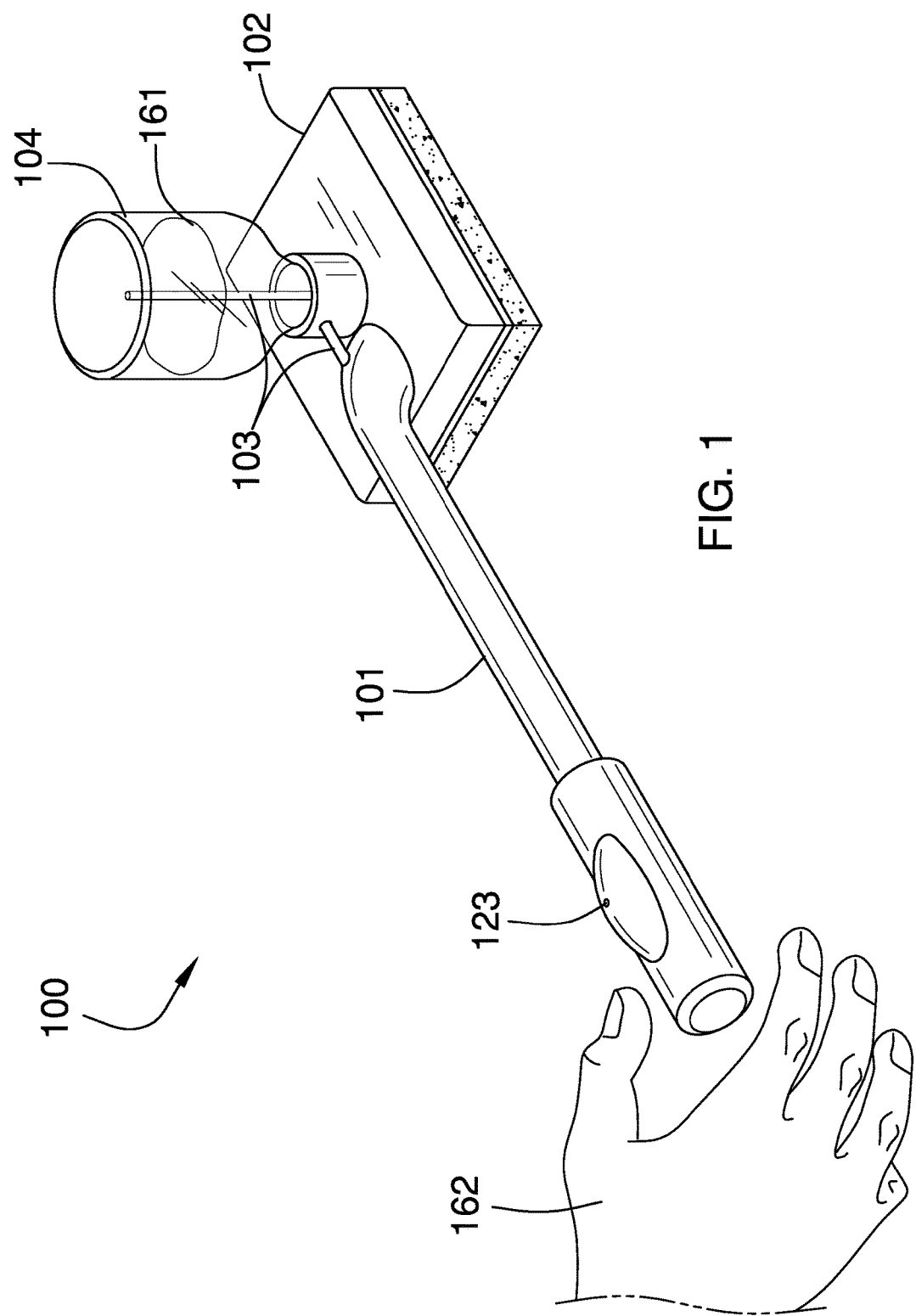
FIG. 1 is a perspective view of an embodiment of the disclosure.
Figure 2:
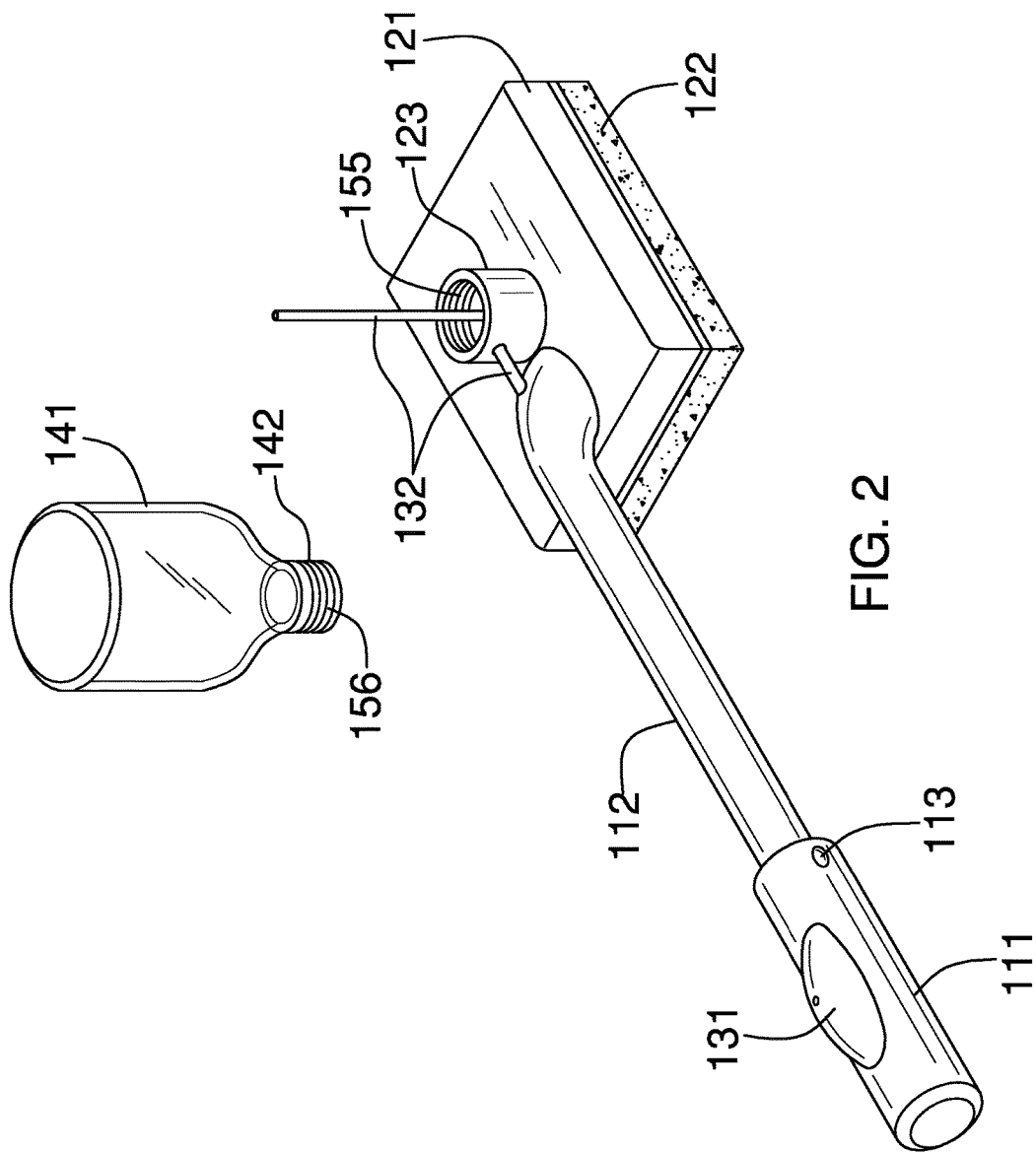
FIG. 2 is an exploded perspective view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 5.

The back cream applicator 100 (hereinafter invention) is configured for use with a therapeutic liquid 161 such as a lotion or cream. The invention 100 applies the therapeutic liquid 161 to a person 162. The invention 100 is configured for self-application of the therapeutic liquid 161. The invention 100 is configured to extend the reach of the person 162 such that the therapeutic liquid 161 can be applied to locations that are otherwise difficult to reach. The invention 100 comprises a telescopic handle 101, a cleansing head 102, a pump 103, and a refillable reservoir 104. The cleansing head 102 applies the therapeutic liquid 161 to the person 162. The refillable reservoir 104 contains a stock of the therapeutic liquid 161 for use by the cleansing head 102. The pump 103 is a mechanical device that transports the therapeutic liquid 161 to the cleansing head 102. The telescopic handle 101 is an extension apparatus that extends the reach of the person 162.

The telescopic handle 101 is an extension apparatus. The telescopic handle 101 extends the reach of the person such that the cleansing head 102 may be placed against hard to reach areas of the person's 162 body. The telescopic handle 101 is a telescopic structure that allows for the span of the length of the telescopic handle 101 to be adjusted.

The telescopic handle 101 further comprises a first arm 111, a second arm 112 and a detent 113. The detent 113 connects the second arm 112 to the first arm 111. The first arm 111 is a hollow first prism that is further defined with an inner dimension. The second arm 112 is a second prism that is further defined with an outer dimension. The first arm 111 and the second arm 112 are geometrically similar. The outer dimension of the second arm 112 is less than the inner dimension of the first arm 111 such that the second arm 112 can be inserted into the first arm 111 in a telescopic manner. This telescopic arrangement of the telescopic handle 101 allows the length of the telescopic handle 101 to be adjusted by adjusting the relative position of the second arm 112 within the first arm 111.

The position of the second arm 112 relative to the first arm 111 is held in position using the detent 113. The detent 113 is a mechanical device that connects and secures the first arm 111 to the second arm 112. In the first potential embodiment of the disclosure, detent 113 is selected from the group consisting of a cotter pin, a G snap collar, a cam lock collar, a threaded clutch, a split collar lock, or a spring loaded ball lock.

The cleansing head 102 is an apparatus that applies the therapeutic liquid 161 to the body of the person 162. The cleansing head 102 comprises a base plate 121 and a cancellated pad 122.

The base plate 121 is a plate structure formed in the manner of a rectangular block. The base plate 121 provides the structural stability of the cleansing head 102 such that the cleansing head 102 may be pressed and rubbed against the body of the person 162 during application of the therapeutic liquid 161. The base plate 121 comprises a threaded fitting 123, and a screen 124.

The cancellated pad 122 attaches to a surface of the base plate 121. The cancellated pad 122 is an elastomeric cancellated structure that: 1) absorbs the therapeutic liquid 161 as the therapeutic liquid 161 is delivered from the pump 103; and, 2) applies the therapeutic liquid 161 to the body of the person 162 as the cancellated pad 122 is pressed against the body of the person 162. A material suitable for use as the cancellated pad 122 includes, but is not limited to, a commercially available sponge. The cancellated pad 122 further comprises a pad frame 126.

Figure 3:
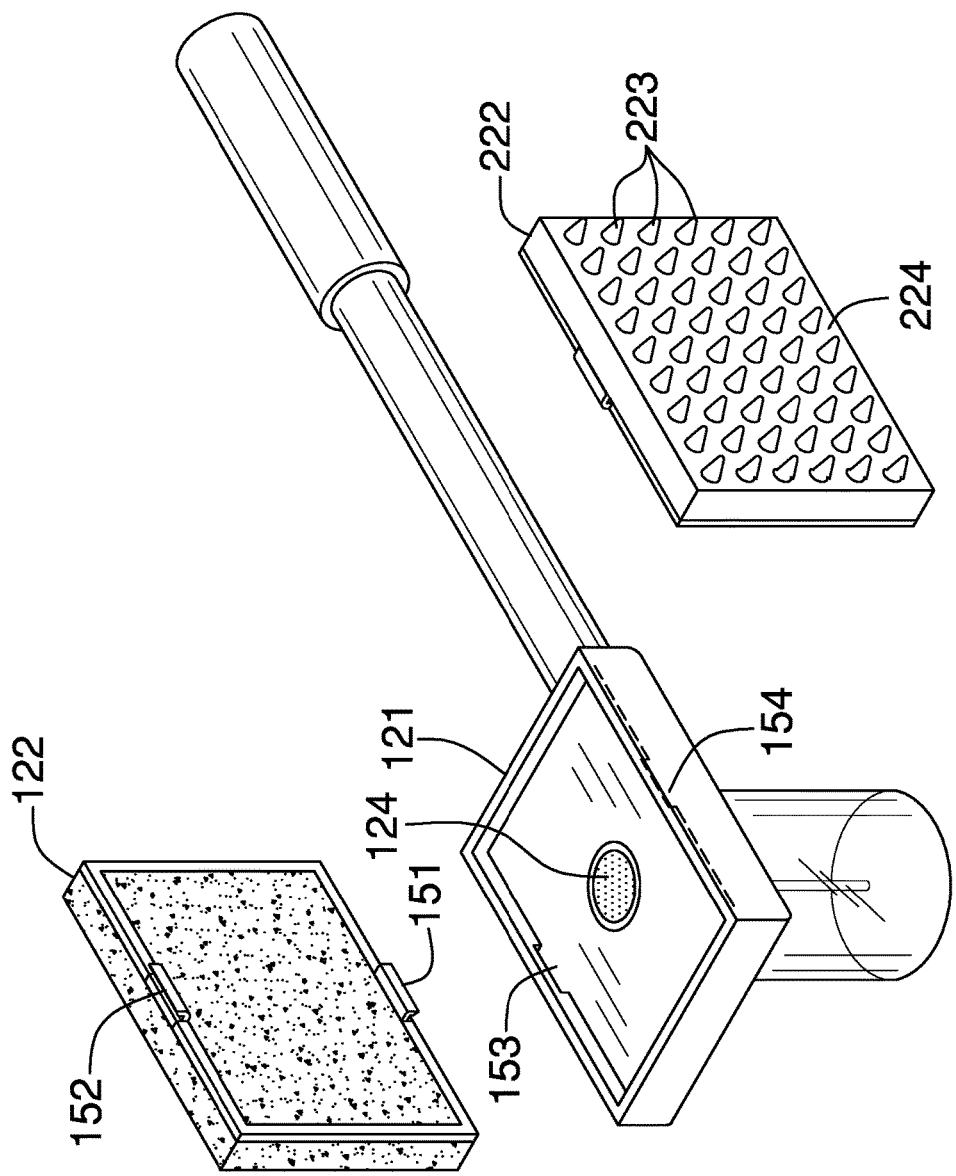
FIG. 3 is a reverse perspective view of an embodiment of the disclosure.

Referring to FIG. 3, the cancellated pad 122 may be interchanged with a second cancellated pad 222. The second cancellated pad 222 is constructed in the same manner as the cancellated pad 122. However, the second cancellated pad 222 includes a plurality of scrubbing nodules 223. The plurality of scrubbing nodules 223 are arranged in an array and provided across a majority of an outer surface 224 of the second cancellated pad 222. The plurality of scrubbing nodules 223 provides a scrubbing effect when in use.

The screen 124 is a mesh structure that is used as a filter. The screen 124 prevents solids from passing into the invention 100 such that the filtered solid cannot inhibit the operation of the invention 100.

The rim 125 is a ridge that is formed around the perimeter of the surface of the base plate 121 upon which the cancellated pad 122 is attached. The rim 125 receives the pad frame 126 for the purpose of attaching the cancellated pad 122 to the base plate 121. The rim 125 further comprises a first latch aperture 153 and a second latch aperture 154.

The threaded fitting 123 is a plumbing fitting that is formed on the surface of the base plate 121 that is distal from the surface upon which the cancellated pad 122 is attached. The threaded fitting 123 is the plumbing fitting that forms a fluid connection between the refillable reservoir 104 and the pump 103. The threaded fitting 123 is formed with an interior screw thread 155 that is used to form a threaded connection with the refillable reservoir 104. The threaded fitting 123 further comprises an interior screw thread 155.

The pad frame 126 is a frame: 1) to which the cancellated pad 122 is removably attached; and, 2) which is removably attachable to the rim 125 of the base plate 121. The perimeter of the pad frame 126 is geometrically similar to the perimeter of the rim 125 such that the pad frame 126 may be inserted within the rim 125. The removable attachment of the pad frame 126 to the rim 125 allows the cancellated pad 122 and the pad frame 126 to be removed from the base plate 121 for maintenance purposes. The removable attachment of the cancellated pad 122 to the pad frame 126 allows the cancellated pad 122 to be replaced for hygienic purposes.

The pad frame 126 further comprises a first locking tab 151 and a second locking tab 152. As shown most clearly in FIG. 3, the first locking tab 151 is a locking tab that is attached to the pad frame 126. The second locking tab 152 is a locking tab that is attached to the pad frame 126. The structure and use of locking tabs are discussed in greater detail elsewhere in this disclosure. The first latch aperture 153 is an aperture that is formed within the rim 125. The first latch aperture 153 is sized to receive the first locking tab 151. The second latch aperture 154 is an aperture that is formed within the rim 125. The second latch aperture 154 is sized to receive the second locking tab 152.

To attach the cancellated pad 122 to the base plate 121, the first locking tab 151 is inserted into the first latch aperture 153 while simultaneously the second locking tab 152 is inserted into the second latch aperture 154. To detach the cancellated pad 122 from the base plate 121, the pad frame 126 is squeezed such that the first locking tab 151 is released from the first latch aperture 153 and the second locking tab 152 is released from the second latch aperture 154 simultaneously.

The pump 103 is a hand operated mechanical device. The pump 103 transports the therapeutic liquid 161 from the refillable reservoir 104 to the cleansing head 102 in preparation for application. In the first potential embodiment of the disclosure, the pump 103 is a commercially available universal dispenser pump that is similar to what is often and commonly referred to as a shampoo pump.

The pump 103 comprises an activator 131 and a tubing 132. The activator 131 is a mechanical device that is operated by the person. The activator 131 is a mechanical device that generates the air pressure differentials used by the pump 103 to transport the therapeutic liquid 161 from the refillable reservoir 104 to the cleansing head 102. The tubing 132 refers to a network of tubes that physically transport the therapeutic liquid 161 through the pump 103 to the cancellated pad 122. Methods to design, source and install the pump 103 as described in this paragraph are well known and documented in the mechanical arts.

The refillable reservoir 104 is a container within which a stock of the therapeutic liquid 161 is stored before transport to the cleansing head 102. The refillable reservoir 104 comprises a bottle 141 and a threaded neck 142.

The exterior screw thread 156 is joined to the interior screw thread 155 to form a threaded connection that attaches the refillable reservoir 104 to the cleansing head 102.

The bottle 141 is a commercially available bottle within which the therapeutic liquid 161 is stored. The threaded neck 142 is the opening of the bottle 141 into and from which the therapeutic liquid 161 is respectively introduced and removed. The threaded neck 142 is formed with an exterior screw thread 156. The threaded neck 142 is sized to fit within the interior screw thread 155 of the threaded fitting 123. The threaded neck 142 screws into the threaded fitting 123 to form a threaded connection.

The following definitions were used in this disclosure:

Bottle: As used in this disclosure, a bottle is a container used for the storage of fluids. Access to the interior of a bottle is gained through the neck of the bottle. The neck is an elongated tube that forms an aperture through which fluids can be introduced and removed from the bottle.

Cancellated: As used in this disclosure, cancellated is used as an adjective to describe a sponge like, net like, or screen like structure.

Congruent: As used in this disclosure, congruent is a term that compares a first object to a second object. Specifically, two objects are said to be congruent when: 1) they are geometrically similar; and, 2) the first object can be superimposed over the second object such that the first object aligns, within manufacturing tolerances, with second object.

Correspond: As used in this disclosure, the term correspond means that a first object is in some manner linked to a second object in a one to one relationship.

Detent: As used in this disclosure, a detent is a device for attaching a first object to a second object in a detachable manner such that: 1) the position of the first object relative to the second object is adjustable; and, 2) the first object is attached to the second object in a detachable manner.

Elastic: As used in this disclosure, an elastic is a material or object that deforms when a force is applied to it and that is able to return to its relaxed shape after the force is removed. A material that exhibits these qualities is also referred to as an elastomeric material.

Extension Apparatus: As used in this disclosure, an extension apparatus is a mechanical structure that is used to extend the span of the distance between any two objects or the reach of a first object towards a second object.

Exterior Screw Thread: An exterior screw thread is a ridge wrapped around the outer surface of a tube in the form of a helical structure that is used to convert rotational movement into linear movement.

Filter: As used in this disclosure, a filter is a mechanical device that is used to separate solids that are suspended in a liquid or a gas.

Fluid: As used in this disclosure, a fluid refers to a state of matter wherein the matter is capable of flow and takes the shape of a container it is placed within. The term fluid commonly refers to a liquid or a gas.

Geometrically Similar: As used in this disclosure, geometrically similar is a term that compares a first object to a second object wherein: 1) the sides of the first object have a one to one correspondence to the sides of the second object; 2) wherein there is a proportional difference between each pair of corresponding sides is the same; 3) the angles formed by the first object have a one to one correspondence to the angles of the second object; and, 4) wherein the corresponding angles are equal.

Inner Dimension: As used in this disclosure, the term inner dimension describes the span from a first inside or interior surface of a container to a second inside or interior surface of a container. The term is used in much the same way that a plumber would refer to the inner diameter of a pipe.

Interior Screw Thread: An interior screw thread is a groove that is formed around the inner surface of a tube in the form of a helical structure that is used to convert rotational movement into linear movement.

Liquid: As used in this disclosure, a liquid refers to a state of matter that is fluid and that maintains, for a given pressure, a fixed volume that is independent of the volume of the container.

Mesh: As used in this disclosure, the term mesh refers to an openwork fabric made from threads, yarns, cords, wires, or lines that are woven, knotted, or otherwise twisted or intertwined at regular intervals. Synonyms for mesh include net.

One to One: When used in this disclosure, a one to one relationship means that a first element selected from first set is in some manner connected to only one element of a second set. A one to one correspondence means that the one to one relationship exists both from the first set the second set and from the second set to the first set. A one to one fashion means that the one to one relationship exists in only one direction.

Openwork: As used in this disclosure, the term open work is used to describe a structure, often a surface, which is formed with openings that allow for visibility and airflow through the structure. Wrought work is a form of openwork.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Perimeter: As used in this disclosure, a perimeter is one or more curved or straight lines that bounds an enclosed area on a plane or surface. The perimeter of a circle is commonly referred to as a circumference.

Plate: As used in this disclosure, a plate is a smooth, flat and rigid object that has at least one dimension that: 1) is of uniform thickness; and 2) that appears thin relative to the other dimensions of the object. Plates often have a rectangular or disk like appearance. As defined in this disclosure, plates may be made of any material, but are commonly made of metal.

Prism: As used in this disclosure, a prism is a 3 dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called that lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous the center axis of a cylinder. A prism wherein the ends are circles is commonly referred to as a cylinder.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Rectangular Block: As used in this disclosure, a rectangular block refers to a three dimensional structure comprising six rectangular surfaces formed at right angles. Within this disclosure, a rectangular block may further comprise rounded edges and corners.

Rim: As used in this disclosure, a rim is an outer edge or border that follows along the perimeter of an object.

Rounded: A used in this disclosure, the term rounded refers to the replacement of an apex, vertex, or edge or brink of a structure with a (generally smooth) curvature wherein the concave portion of the curvature faces the interior or center of the structure.

Screen: As used in this disclosure, a screen is a meshed structure made or wire or yarn wire or cloth that allows for the free flow of fluid but prevents larger objects from passing through the meshed structure.

Screw: When used as a verb in this disclosure, to screw means: 1) to fasten or unfasten (unscrew) a threaded connection; or 2) to attach a helical structure to a solid structure.

Telescopic: As used in this disclosure, telescopic is an adjective that describes an object made of sections that fit or slide into each other such that the object can be made longer or shorter by adjusting the relative positions of the sections.

Therapeutic: As used in this disclosure, therapeutic is an adjective that refers to a medical, ameliorative, or hygienic substance, process, or procedure.

Threaded Connection: As used in this disclosure, a threaded connection is a type of fastener that is used to join a first tube shaped and a second tube shaped object together. The first tube shaped object is fitted with fitted with a first fitting selected from an interior screw thread or an exterior screw thread. The second tube shaped object is fitted with the remaining screw thread. The tube shaped object fitted with the exterior screw thread is placed into the remaining tube shaped object such that: 1) the interior screw thread and the exterior screw thread interconnect; and, 2) when the tube shaped object fitted with the exterior screw thread is rotated the rotational motion is converted into linear motion that moves the tube shaped object fitted with the exterior screw thread either into or out of the remaining tube shaped object. The direction of linear motion is determined by the direction of rotation.

Universal Dispenser Pump: As used in this disclosure, a universal dispenser pump is a pump that is used to pump a liquid out of a bottle. The universal dispenser pump is a well-known and documented commercially available product that is often referred to as a soap pump or a shampoo pump.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:
1. A therapeutic applicator comprising:
a handle, a cleansing head, a pump, and a refillable reservoir;
wherein the refillable reservoir contains a stock of the therapeutic liquid for use by the cleansing head;
wherein the pump is a mechanical device that transports the therapeutic liquid to the cleansing head;
wherein the therapeutic applicator is configured for use with a therapeutic liquid;
wherein the therapeutic applicator is adapted to apply the therapeutic liquid to a body of a person;
wherein the therapeutic applicator is configured for self-application of the therapeutic liquid to the person;
wherein the therapeutic applicator is configured to extend a reach of the person;
wherein the cleansing head applies the therapeutic liquid to the person;
wherein the handle is further defined with a length;
wherein the pump is a hand operated mechanical device;
wherein the pump transports the therapeutic liquid from the refillable reservoir to the cleansing head;
wherein the refillable reservoir is a container within which a stock of the therapeutic liquid is stored;
wherein the handle further comprises a first arm, and a second arm;
wherein the first arm is a hollow first prism that is further defined with an inner dimension;
wherein the second arm is a second prism that is further defined with an outer dimension;
wherein the first arm and the second arm are geometrically similar;
wherein the cleansing head comprises a base plate and a cancellated pad;
wherein the cancellated pad removably attaches to the base plate;
wherein the base plate is a plate structure;
wherein the base plate provides adequate structural stability to the cleansing head such that the cleansing head is adapted to be pressed and rubbed against the body of the person;
wherein the base plate comprises a threaded fitting, a screen, and a rim;
wherein the rim is a ridge that is formed around the perimeter of the base plate;
wherein the screen is a mesh that forms a filter.

2. The therapeutic applicator according to claim 1 wherein the cancellated pad is an elastomeric cancellated structure;
wherein the cancellated pad absorbs the therapeutic liquid as the therapeutic liquid is delivered from the pump;
wherein the cancellated pad applies the therapeutic liquid to the body of the person as the cancellated pad.

3. The therapeutic applicator according to claim 2
wherein the cancellated pad further comprises a pad frame;
wherein the pad frame attaches the cancellated pad to the base plate;
wherein the rim receives the pad frame.

4. The therapeutic applicator according to claim 3
wherein the threaded fitting is formed on the surface of the base plate that is distal from the surface upon which the rim is formed;
wherein the threaded fitting further comprises an interior screw thread.

5. The therapeutic applicator according to claim 4 wherein the pad frame is a frame to which the cancellated pad is removably attached.

6. The therapeutic applicator according to claim 5 wherein the pad frame is removably attachable to the rim of the base plate.

7. The therapeutic applicator according to claim 6 wherein the perimeter of the pad frame is geometrically similar to the perimeter of the rim such that the pad frame may be inserted within the rim.

8. The therapeutic applicator according to claim 7
wherein the pad frame further comprises a first locking tab and a second locking tab;
wherein the first locking tab attaches to the pad frame;
wherein the second locking tab attaches to the pad frame.

9. The therapeutic applicator according to claim 8
wherein the rim further comprises a first latch aperture and a second latch aperture;
wherein the first latch aperture is an aperture that is formed within the rim;
wherein the second latch aperture is an aperture that is formed within the rim;
wherein the first latch aperture is sized to receive the first locking tab;
wherein the second latch aperture is sized to receive the second locking tab.

10. The therapeutic applicator according to claim 9
wherein the first locking tab inserts into the first latch aperture;
wherein the second locking tab inserts into the second latch aperture.

11. The therapeutic applicator according to claim 10
wherein the pump comprises an activator and a tubing;
wherein the activator is a mechanical device that is operated by the person;
wherein the activator is a mechanical device that generates an air pressure differential.

12. The therapeutic applicator according to claim 11
wherein the refillable reservoir comprises a bottle and a threaded neck;
wherein the threaded neck is formed with an exterior screw thread;
wherein the threaded neck is sized to fit within the interior screw thread of the threaded fitting;
wherein the exterior screw thread is joined to the interior screw thread to form a threaded connection that attaches the refillable reservoir to the cleansing head.

13. The therapeutic applicator according to claim 12, a second cancellated pad is provided and used in lieu of the cancellated pad; wherein the second cancellated pad includes a plurality of scrubbing nodules; wherein the plurality of scrubbing nodules are arranged in an array and provided across a majority of an outer surface of the second cancellated pad; wherein the plurality of scrubbing nodules provides a scrubbing effect when in use.

* * * * *